United States Patent [19]

Krüger et al.

[11] 4,358,408

[45] Nov. 9, 1982

[54] PROPANE-1,2-DIONEDIOXIMES, PESTICIDES CONTAINING THESE COMPOUNDS, AND THE METHOD FOR THEIR PREPARATION

[75] Inventors: Hans R. Krüger; Hartmut Joppien, both of Berlin, Fed. Rep. of Germany

[73] Assignee: Schering AG, Berlin and Bergkamen, Fed. Rep. of Germany

[21] Appl. No.: 150,172

[22] Filed: May 15, 1980

Related U.S. Application Data

[63] Continuation of Ser. No. 793,577, May 4, 1977, abandoned.

[30] Foreign Application Priority Data

May 10, 1976 [DE] Fed. Rep. of Germany ....... 2621102

[51] Int. Cl.$^3$ ............................................ C07C 131/00
[52] U.S. Cl. ............................. 260/453.3; 260/404.5; 260/463; 260/464; 260/465.4; 260/465 D; 260/455 B; 424/298; 424/301; 424/304
[58] Field of Search .............. 260/453.3, 404.5, 469.3; 424/298

[56] References Cited

U.S. PATENT DOCUMENTS

| | | | |
|---|---|---|---|
| 3,231,599 | 1/1966 | Kilsheimer et al. | 260/464 |
| 3,506,698 | 4/1970 | Jeliner | 260/453 RW |
| 3,576,834 | 4/1971 | Buchanan | 260/453 RW |
| 3,657,307 | 4/1972 | Summers | 260/453 R |
| 3,832,375 | 8/1974 | Itoh | 260/463 |
| 3,901,683 | 8/1975 | Limpel et al. | 71/98 |
| 4,029,688 | 6/1977 | D'Silva | 260/465.4 |
| 4,052,194 | 10/1977 | Wilcox | 71/121 |
| 4,096,166 | 6/1978 | Alvarez et al. | 260/453 RW |
| 4,118,389 | 10/1978 | Magee | 424/298 UX |

FOREIGN PATENT DOCUMENTS

| | | |
|---|---|---|
| 674792 | 5/1966 | Belgium . |
| 2036491 | 1/1972 | Fed. Rep. of Germany . |
| 2216838 | 11/1972 | Fed. Rep. of Germany . |
| 2409463 | 9/1975 | Fed. Rep. of Germany . |

*Primary Examiner*—Joseph Paul Brust
*Attorney, Agent, or Firm*—Michael J. Striker

[57] ABSTRACT

The invention concerns the preparation of new propane-1,2-dionedioximes, particularly pesticides having an insecticidal action containing these compounds as active substance, and to methods for the preparation of these compounds.

1 Claim, No Drawings

PROPANE-1,2-DIONEDIOXIMES, PESTICIDES CONTAINING THESE COMPOUNDS, AND THE METHOD FOR THEIR PREPARATION

This is a continuation, of application Ser. No. 793,577, filed May 4, 1977, now abandoned.

It is known that oxime carbamates have been used as pesticides (Cf. DOS 2,409,463, DOS 2,036,491, DOS 2,216,838, and Belgian patent 674,792). These oxime carbamates have a wide spectrum in their insecticidal, acaricidal and nematicidal properties.

With the above in view it is an object of the present invention to provide a preparation which permits the selective control of harmful insects.

This problem is solved according to the invention by a preparation which is characterized by a content of at least one propane-1,2-dionedioxime of the general formula

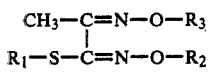      I where
$R_1$ denotes a $C_1$–$C_4$ alkyl radical or ethyl cyanide ($C_2H_5CN$);

$R_2$ and $R_3$ each represent hydrogen, the methyl carbamoyl group or the radical

where $R_4$ represents a $C_1$–$C_{11}$ alkyl radical, a substituted $C_1$–$C_{11}$ alkyl radical, a $C_5$–$C_8$-cycloaliphatic hydrocarbon radical, a $C_5$–$C_8$-cycloaliphatic hydrocarbon radical mono- or poly-substituted by $C_1$–$C_6$-alkyl, an aromatic hydrocarbon radical, an aromatic hydrocarbon radical, mono- or polysubstituted by $C_1$–$C_6$-alkyl and/or halogen and/or $C_1$–$C_6$-alkoxy and/or the nitro group, a $C_1$–$C_6$-alkoxy group or a $C_1$–$C_4$-alkylthio-group or an amino group

where $R_5$ and $R_6$ each denotes hydrogen, $C_1$–$C_6$-alkyl, aryl or aryl mono- or polysubstituted, in an identical or different manner, by $C_1$–$C_6$-alkyl, halogen, $C_1$–$C_6$-alkoxy, the nitro group and/or the trifluormethyl group, where at least one of the radicals $R_2$ or $R_3$ represents the methylcarbamoyl group.

The compounds according to the present invention show surprisingly a selective action against insects, which opens up in an advantageous manner the possibility of controlling these pests without interfering widely with the treated biotopes and their biozoenoses.

The propane-1,2-dionedioxmes according to the invention act against the postembryonal development stages of beetles and/or flies and/or aphids, and show an infestation-inhibiting characteristic effect after the application of low concentrations. In an advantageous manner the compounds according to the invention penetrate through the leaves and roots into the plants and thus display an additional systemic action.

The compounds according to the invention have a good initial and permanent effect on the treated pest population in applications between about 0.1 and 1.0 kg active substance per hectare. The reduced initial effect with low concentrations is compensated by a clear reduction of the eating-activity of harmful biting insects.

The compounds are highly compatible with plants, such as sugar beets, cotton, barley, corn, tomatoes and other vegetables or cultures.

The compounds according to the invention can be used either per se or mixed with each other or with other insecticides in desired proportions. If necessary, other plant protectives or pesticides, such as acaricides or fungicides, can be added, depending on the intended purpose.

The action or the rate of action can be increased by the use of action-increasing additives, such as organic solvents, wetting agents and oils. These additions therefore permit the reduction of the dosage of the active substances.

The above mentioned active substances or mixtures thereof are preferably used in the form of preparations, such as powders, dusting powders, granules, solutions, emulsions or suspensions, by adding liquid and/or solid vehicles or diluents, and, if necessary, crosslinking-, adhesive-, emulsifying- and/or dispersing agents. Suitable liquid vehicles that may be used are water, aliphatic and aromatic hydrocarbons, such as benzene, toluene, xylene, cyclohexanone, isophorone, dimethyl sulfoxide, dimethyl formamide, or other mineral oil fractions.

Solid vehicles suitable for use are, for example, siliceous clay, silica gel, talcum, kaolin, atta clay, limestone, silica and plant products such as flours.

Suitable surface-active substances are, for example: calcium lignin sulfonate, polyoxyethylene-alkyl phenylether, naphthalene sulfonic acids and their salts, phenolsulfonic acids and their salts, formaldehyde condensates, fatty alcohol sulfates as well as substituted benzene sulfonic acids and their salts.

The portion of the active substance(s) in the various preparations can vary within wide limits. For example, the preparation can contain about 10 to 80% by weight of active substances, about 90 to 20% by weight liquid or solid vehicles, as well as up to 20% surface-active substances if necessary.

The preparation can be dispensed in the usual known manner. For example, with water as a vehicle, by spraying in amounts of about 100 to 1000 liter/ha. Application of the preparation in the so-called "low-volume" and "ultra low volume" method is likewise possible, as well as application in the form of so-called microgranules.

These preparations can be produced in the usual known manner, for example, by mixing or grinding. If desired, the individual components can be mixed briefly before use, as it is done in practice, for example, in the so-called tankmixing method.

Of the compounds according to the invention, those are particularly characterized by superior action where $R_1$ in the general formula represents a methyl group, $R_2$ a methylcarbamoyl group and $R_3$ the indicated meaning in the above formula I.

Among the radicals designated with $R_4$ in the general formula, are for example: $C_1$–$C_{11}$-alkyl radicals, like methyl, ethyl, propyl, n-butyl-1-ethyl-propyl, tertiary butyl, n-heptyl, n-nonyl, n-undecyl and 3,3-dimethyl-propyl; $C_5$–$C_8$-cycloaliphatic hydrocarbon radicals like cyclopentyl, cyclohexyl and methylcyclohexyl, aromatic hydrocarbon radicals, like phenyl and substituted aromatic hydrocarbon radicals, such as, 3-chlorophenyl, 4-chlorophenyl, 2,4-dichlorophenyl, 2-methylphenyl, 3-methylphenyl, 4-methylphenyl, 3-nitrophenyl, 4-nitrophenyl, 2-methoxyphenyl and 4-methoxyphenyl; $C_1$–$C_6$-alkoxy radicals, like methoxy, ethoxy, propoxy and isopropoxy; $C_1$–$C_4$-alkylthio radicals like methylthio, ethylthio and propylthio, and amino groups, like methylamino, dimethylamino, propylamino and 4-chloroanilino.

The compounds according to the invention can be prepared according to the following methods, where $R_1$, $R_2$, $R_3$, $R_4$, $R_5$ and $R_6$ have the above indicated meaning and X represents a halogen atom.

Method A.a.

This method can be represented by the following reaction pattern:

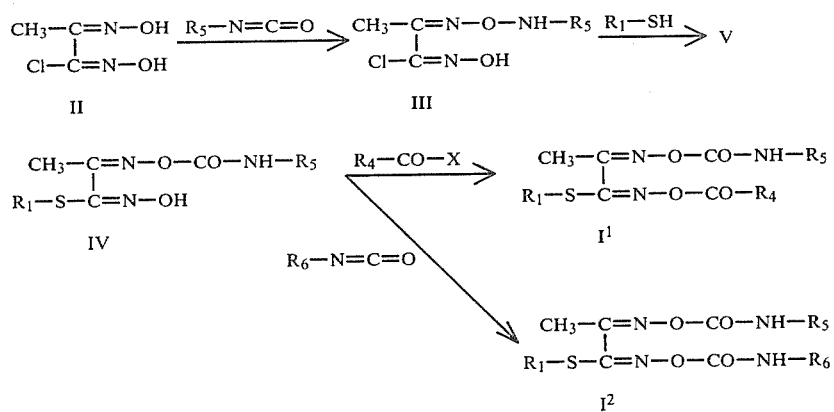

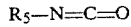

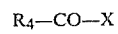

Method A.b.

This method can be represented by the following reaction pattern:

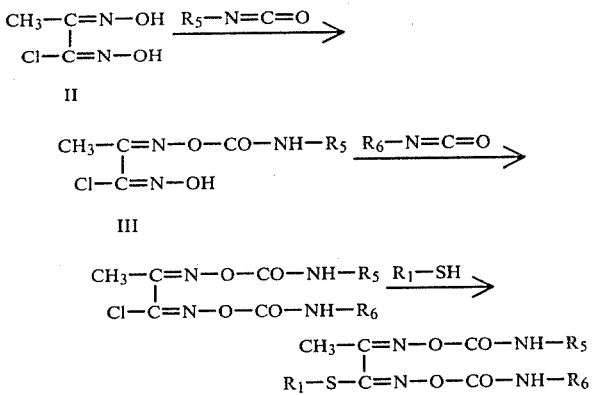

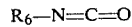

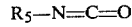

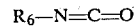

The synthesis of the compounds I according to the invention is effected by starting from known 1-chloropropane-1,2-dionedioxime (II), by reacting it with isocyanates of the general formula $R_5$—N=C=O in organic solvents, such as tetrahydrofuran and chlorinated hydrocarbons, in the presence of a catalyst, preferably an organic base, such as triethylamine to the isolable compounds III, which are reacted with mercaptans of the general formula $R_1$—SH in the presence of an acid acceptor, such as tertiary amine, like triethyl amine, N,N-dimethylaniline, pyridine-bases or suitable inorganic bases, like oxides, hydroxides or carbonates of the alkali or alkaline earth metals or preferably alcoholates, or with alkali- or alkaline earth salts of the above mentioned mercaptans in organic solvents to the formula IV compounds.

These can then be reacted with acyl halides of the general formula $R_4$—CO—X in the presence of an acid acceptor or with isocyanates of the general formula $R_6$—N=C=O 1-Chloropropane-1,2-dionedioxime (II) is thus reacted, as in method A.a. with an isocyanate of the general formula $R_5$—N=C=O to the compounds III.

III can be reacted under suitable conditions, for example, in dimethyl formamide in the presence of hexamethyl phosphoric triamides as a catalyst with another mole of identical or non-identical isocyanate of the general formula $R_6$—N=C=O The resulting compounds (V) can then be reacted with mercaptans of the general formula $R_1$—SH in the presence of an acid acceptor, for example, tertiary amines, like triethylamine, N,N-dimethylaniline, pyridine bases, or suitable inorganic bases, like oxides or hydroxides or carbonates of the alkali- or alkaline earth metals, or preferably alcoholates, or with alkali- or alkaline earth salts of the above mentioned mercaptans in organic solvents, preferably alcohols to the desired compounds $I^2$ according to the invention.

In the case of identical isocyanates, the preparation is preferably produced by reacting 1-chloropropane-1,2-dionoxide under suitable conditions, for example in dimethylformamide in the presence of hexamethylphosphoric triamide as a catalyst with 2 moles of the same isocyanate.

Method A.c.

This method can be represented by the following reaction pattern:

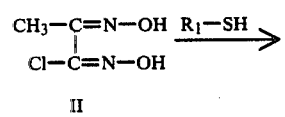

II

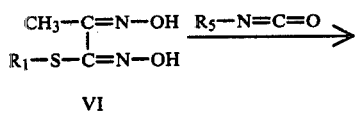

VI

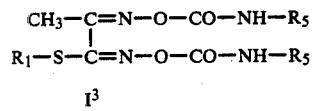

$I^3$

1-Chloropropane-1,2-dionedioxim (II) is thus reacted with mercaptans of the general formula

in an organic solvent in the presence of an acid acceptor, for example, tertiary amines, like triethyl amine, N,N-dimethylaniline, pyridine bases, or suitable inorganic bases, like oxides, hydroxides or carbonates of the alkali- or alkaline earth metals or preferably alcoholates, or with alkali- or alkaline earth salts of the above mentioned mercaptans to the 1-alkylthiopropane-1,2-dionedioximes (VI).

VI reacts with isocyanates of the general formula

in organic solvents in the presence of a catalyst, preferably an organic base to the compounds $I^3$ according to the invention.

Method A.d.

This method can be represented by the following reaction pattern:

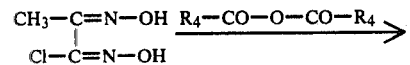

II

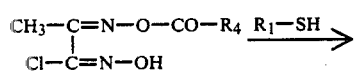

VII

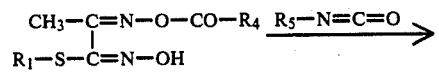

VIII

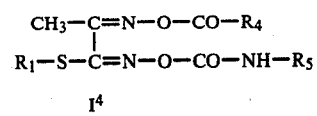

$I^4$

1-Chloropropane-1,2-dionedioxim (II) is thus reacted with acid anhydrides of the general formula $$R_4-CO-O-CO-R_4$$

in organic solvents, if necessary, in the presence of an acid catalyst, to the compounds (VII), which react with mercaptans of the general formula $$R_1-SH$$

in the presence of an acid acceptor, dissolved in organic solvents, to the compounds (VIII).

Compounds of formula VIII can then be reacted with isocyanates of the general formula $$R_5-N=C=O$$

in organic solvents in the presence of a catalyst to the compounds $I^4$ according to the invention.

Method B.

This method can be represented by the following reaction pattern:

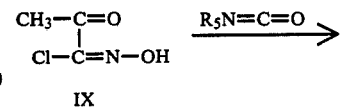

IX

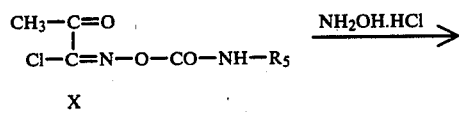

X

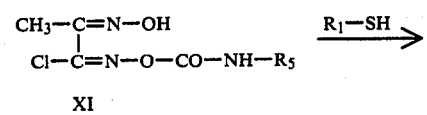

XI

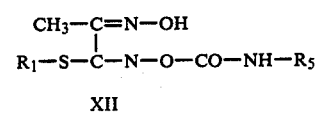

XII

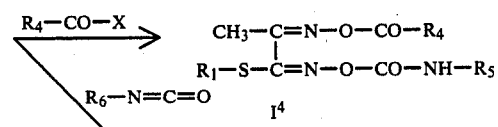

$I^4$

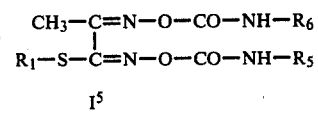

$I^5$

The known 1-chloropropane-1,2-dione-1-oxim (IX) is thus reacted with isocyanates of the general formula $$R_5-N=C=O$$

in organic solvents in the presence of a catalyst to the compounds (X).

The compounds of the general formula X can then be reacted with hydroxylamine hydrochloride, preferably in aqueous solution, to the compounds (XI), which in turn react with mercaptans of the general formula $$R_1-SH$$

in the presence of an acid acceptor, dissolved in organic solvents, to the compounds (XII).

These can be reacted with acyl halides of the general formula $$R_4-CO-X$$

in the presence of an acid acceptor or with isocyanates of the general formula $$R_6-N=C=O$$

in the presence of a catalyst to the compounds I$^4$ or I$^5$ according to the invention.

The liquid or solid propane-1,2-dionedioximes prepared according to the above mentioned methods can be isolated from the reaction mixture by known methods, for example, by distilling off the solvents at normal or reduced pressure.

Though very pure propane-1,2-dionedioximes are obtained with this method, they can be further purified, for example, by recrystallization or by chromatography.

The propane-1,2-dionedioximes according to the invention represent colorless and odorless crystalline substances or oils which are soluble with difficulty in aliphatic hydrocarbons, easily soluble in polar organic solvents, like ketones, carboxylic amides, such as dimethyl formamide, sulfoxides, like dimethyl sulfoxides, carboxylic nitrides, low alcohols, halogenated hydrocarbons, and are conditionally soluble in water.

The following examples will illustrate the preparation of the compounds according to the invention. The starting products for the preparation of the compounds are known in themselves or can be prepared according to known methods, as described in the examples.

Example 1 (Method A.d)

2-methyl-1-methylthio-O-methylcarbamoyl-O'-methylcarbonylglyoxime $$CH_3-C=N-O-CO-CH_3$$
$$CH_3-S-C=N-O-CO-NH-CH_3$$

9.5 g (0.05 mde) 2-methyl-1-methylthio-O'-methylcarbonylglyoxime are suspended in 50 ml methylene chloride and mixed with 4 ml (0.06 mole) methyl isocyanate, and the mixture is left standing for 48 hours at room temperature. After removal of the solvent, the mixture is digested with pentane.

Yield: 12.0 g = 94.5% of the theory
$n_D^{20} = 1.5248$.

Starting Products for the Preparation of Compound No. 1

(1)

2-methyl-1-methylthio-O'-methylcarbonyl-glyoxime;

$$CH_3-C=N-O-CO-CH_3$$
$$CH_3S-C=N-OH$$

A solution of 52.55 g (0.3 mole) 2-methyl-1-chloro-O'-methylcarbonyl-glyoxime in 600 ml tetrahydrofuran is cooled to 0° C. and mixed with 25 ml (0.46 mole) methylmercaptan. Under stirring and cooling are added slowly in drops 40.8 ml (0.3 mole) triethylamine. The stirring is continued for 1 hour at 0° C., then for 3 hours at 50° C., and the mixture is left standing over night at room temperature. The precipitate is sucked off, the filtrate concentrated, and the oily residue digested with pentane. Recrystallization from methanol. Yield: 54.4 g = 95.5% of the theory Melting point: 121°-123° C.

(2) 2-methyl-1-chloro-O'-methylcarbonyl-glyoxime $$CH_3-C=N-O-CO-CH_3$$
$$Cl-C=N-OH$$

68.0 g (0.5 mole) 1-chloropropane-1,2-dionedioxime are suspended in 500 ml ether and mixed under stirring with 47.5 ml (0.5 mole) acetanhydride at room temperature.

The mixture is stirred for 7 hours, and left standing for 48 hours. The precipitate is sucked off, the filtrate concentrated, the resulting crystals combined and washed with some cold ether. Recrystallization from acetonitrile.

Yield: 71.3 g = 80% of the theory
Melting point: 165°-168° C.

EXAMPLE 2

In the open land the larvae of the potato beetle (leptinotarsa decemlineata) were counted within the test lots on infested, marked potato plants before the treatment, as well as on the first, fourth and seventh day after the treatment. The effectiveness of the preparation was calculated according to the formula by Schneider-Orelli.

The amount used per preparation was 288 g active substance per ha in 480 liters of water.

TABLE 3

|  | Effectiveness in % | | |
| --- | --- | --- | --- |
|  | 1 day | 4 days | 7 days |
|  |  | after spraying |  |
| Compound according to the invention |  |  |  |
| 2-methyl-1-methylthio-O—methylcarbamoyl-O'—methylcarbonyl-glyoxime | 85 | 76 | 74 |
| 2-methyl-1-methylthio-O—methylcarbamoyl-O'—ethylcarbonyl-glyoxime | 62 | 70 | 82 |
| 2-methyl-1-methylthio-O,O'—bis-methylcarbamoyl-glyoxime | 95 | 93 | 94 |
| Reference compound |  |  |  |
| S—methyl-N—[(methylcarbamoyl)-oxy]-thioacetimidate (according to Belgian Patent 674,792) | 31 | 68 | 47 |

EXAMPLE 3

In the open land the number of beetles was counted within the test lots on marked potato plants infested with adult potato beetles (leptinotarsa decemlineata) before the treatment, as well as on the 1st, 4th and 7th day after the treatment. The effectiveness was calculated according to the formula by Schneider-Orelli.

The amount used per preparation was 288 g active substance per ha in 480 liter water.

TABLE 4

|  | effectiveness in % | |
|---|---|---|
|  | 1st day | 4 days |
| Compound according to the invention | | |
| 2-methyl-1-methylthio-O—methylcarbamoyl-O'—methylcarbonyl-glyoxime | 82 | 87 |
| 2-methyl-1-methylthio-O,O'—bis-methylcarbamoyl-glyxime | 93 | 74 |
| Reference compound | | |
| S—methyl-N—[(methylcarbamoyl)-oxy]-thioacetimidate (according to Belgian Patent 674,792) | 75 | 56 |

For synthesing the compounds according to the invention are used acid acceptors selected from the group consisting of organic or in organic bases, such as triethyl amine, N,N-dimethylaniline, pyridine, potassium carbonate, magnesium oxide; and catalysts selected from the group consisting of bases or acids, such as triethyl amine, N,N-dimethylaniline pyridine, hexamethylphosphoric acid triamide, p-toluenesulphonic acid, sulphuric acid, hydrochloric acid.

We claim:

1. 2-methyl-1-methylthio-O-methylcarbamoyl-O'-methylcarbonylglyoxime.

* * * * *